United States Patent
Gisler et al.

(10) Patent No.: US 11,389,987 B2
(45) Date of Patent: Jul. 19, 2022

(54) HYBRID SAW BLADE (71) Applicant: SYNTHES GMBH, Oberdorf (CH)

(72) Inventors: Stefan Gisler, Zuchwil (CH); Bruno Alessandri, Zuchwil (CH)

(73) Assignee: Synthes GmbH, Oberdorf (CH)

( * ) Notice: Subject to any disclaimer, the term of this patent is extended or adjusted under 35 U.S.C. 154(b) by 0 days.

(21) Appl. No.: 16/456,457

(22) Filed: Jun. 28, 2019

(65) Prior Publication Data
US 2020/0001494 A1 Jan. 2, 2020

Related U.S. Application Data (60) Provisional application No. 62/692,056, filed on Jun. 29, 2018.

(51) Int. Cl.
*B27B 19/00* (2006.01)
*A61B 17/14* (2006.01)
*B23D 61/00* (2006.01)
*B23D 61/12* (2006.01)

(52) U.S. Cl.
CPC .......... *B27B 19/008* (2013.01); *A61B 17/142* (2016.11); *B23D 61/006* (2013.01); *B23D 61/125* (2013.01); *B23D 61/127* (2013.01)

(58) Field of Classification Search
CPC ... B27B 19/008; B27B 19/006; B23D 61/125; B23D 61/006; B23D 61/127; A61B 17/142; A61B 2017/00964
See application file for complete search history.

(56) References Cited

U.S. PATENT DOCUMENTS

| 5,035,058 | A | * | 7/1991 | Date | B27B 17/025 30/387 |
| 5,569,257 | A | * | 10/1996 | Arnegger | B23D 61/006 30/350 |
| 7,691,106 | B2 | | 4/2010 | Schenberger et al. | |
| 8,734,450 | B2 | * | 5/2014 | Landon | A61B 17/142 30/337 |
| 8,920,424 | B2 | * | 12/2014 | Boykin | A61C 3/12 606/82 |
| 9,242,361 | B2 | * | 1/2016 | Kaye, Jr. | B25F 3/00 |
| 10,220,539 | B2 | * | 3/2019 | Mann | B24D 5/123 |
| 2006/0009796 | A1 | * | 1/2006 | Carusillo | A61B 17/14 606/178 |

(Continued)

FOREIGN PATENT DOCUMENTS

| DE | 103 25 392 A1 | 12/2004 |
| EP | 1 106 318 A2 | 11/2000 |

(Continued)

OTHER PUBLICATIONS

English translation of EP 2 823 777 A1, Jan. 14, 2015.*

(Continued)

*Primary Examiner* — Hwei-Siu G Payer
(74) *Attorney, Agent, or Firm* — Kramer & Amado, P.C.

(57) ABSTRACT

A surgical saw blade including a cutting edge, blade body and a coupling for connecting the blade body to a handpiece. The blade body at least partially includes a composite material that helps to confer optimal weight and rigidity to the saw blade to allow for minimal vibration during use and minimal mechanical load on the handpiece.

10 Claims, 13 Drawing Sheets

(56) References Cited

U.S. PATENT DOCUMENTS

| | | | |
|---|---|---|---|
| 2007/0083209 A1* | 4/2007 | Schenberger | A61B 17/142 606/82 |
| 2008/0027449 A1* | 1/2008 | Gundlapalli | A61B 17/1624 606/82 |
| 2009/0093815 A1* | 4/2009 | Fletcher | B23D 61/121 606/82 |
| 2009/0312761 A1* | 12/2009 | Boykin | B27B 19/006 606/82 |
| 2010/0292701 A1 | 11/2010 | Fisher et al. | |
| 2011/0309589 A1* | 12/2011 | Maras | B25F 3/00 279/143 |
| 2014/0325855 A1* | 11/2014 | Bozic | B27B 19/006 30/392 |
| 2015/0000143 A1* | 1/2015 | Bozic | A61B 17/14 30/347 |
| 2015/0143705 A1* | 5/2015 | Bozic | B23D 51/10 30/166.3 |
| 2016/0158856 A1 | 6/2016 | Wikus-Saegenfabrik | |
| 2017/0100790 A1* | 4/2017 | Rubens | B24B 27/08 |
| 2017/0182570 A1* | 6/2017 | Dvorak | B23D 51/00 |
| 2020/0001494 A1* | 1/2020 | Gisler | B23D 61/006 |

FOREIGN PATENT DOCUMENTS

| | | |
|---|---|---|
| EP | 2 823 777 A1 | 1/2015 |
| WO | WO 2020/003244 A3 * | 1/2020 |

OTHER PUBLICATIONS

English translation of DE 103 25 392 A1, Dec. 23, 2004.*
Notification of Transmittal of the International Search Report and the Written Opinion of the International Searching Authority or the Declaration, dated Jan. 28, 2020 in connection with International Application No. PCT/IB2019/055526, filed Jun. 28, 2019.
Written Opinion of the International Searching Authority, dated Jan. 28, 2020 in connection with International Application No. PCT/IB2019/055526, filed Jun. 28, 2019.

* cited by examiner

HYBRID SAW BLADE

TECHNICAL FIELD

Various exemplary embodiments disclosed herein relate to a hybrid saw blade including a blade body that at least partially includes a composite material.

BACKGROUND

Traditionally, oscillating saw blades, including sagittal saw blades, for surgical applications are manufactured in one piece and preferably made from steel. The saw blades are manufactured using manufacturing methods such as punching, laser cutting, bending, grinding, etching, stamping, etc. and have a wide variety of shapes and geometries.

Sagittal saw blades are often used for osteotomies, wherein the sagittal saw cuts in the same plane as the body of the instrument.

Traditional saw blades are commonly characterized by having more weight with increasing length, width and thickness, which leads to increased noise and vibration levels, as well as to a higher mechanical load on the transmission system, e.g., the handpiece. However, a certain length and thickness is indispensable for the intended use of the saw blades to be fulfilled.

SUMMARY

A brief summary of various exemplary embodiments is presented below. Some simplifications and omissions may be made in the following summary, which is intended to highlight and introduce some aspects of the various exemplary embodiments, but not to limit the scope of the invention. Detailed descriptions of an exemplary embodiment adequate to allow those of ordinary skill in the art to make and use the inventive concepts will follow in later sections.

Various embodiments disclosed herein relate to a saw blade that includes a blade body having a top surface and a bottom surface, wherein the blade body at least partially includes a composite material, a cutting edge on a distal end of the blade body, and a coupling on a proximal end of the blade body configured to connect the blade body to a handpiece adapted to oscillate the blade body.

Various embodiments further relate to a saw blade, wherein the saw blade further includes at least two of the materials selected from a group that includes steel, polymer, titanium and ceramic materials.

Various embodiments further relate to a saw blade, wherein at least one of the top surface and the bottom surface of the blade body includes an inlay portion including a composite material, such as a matrix material, a plastic material, a filling material and/or a carbon fiber fabric material.

Various embodiments further relate to a saw blade system, wherein the composite inlay portion includes a plurality of holes extending along a longitudinal axis of the blade body.

Various embodiments further relate to a saw blade system, wherein the composite inlay portion is surrounded by a metal frame, such as a steel frame.

Various embodiments further relate to a saw blade, wherein the blade body and coupling both include a composite material.

BRIEF DESCRIPTION OF THE DRAWINGS

In order to better understand various exemplary embodiments, reference is made to the accompanying drawings, wherein.

DETAILED DESCRIPTION

The description and drawings illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art, and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various embodiments described herein are not necessarily mutually exclusive, as some embodiments can be combined with one or more other embodiments to form new embodiments.

The present disclosure provides for a hybrid saw blade 100 manufactured from a combination of different materials. The weight and rigidity of the blade body 120 of the saw blade 100 is optimized in such a way that the vibration and noise load on the user as well as the mechanical load on any attached handpiece (transmission system) of an oscillating saw blade system are as low as possible without negatively affecting clinical output.

Figure 1:
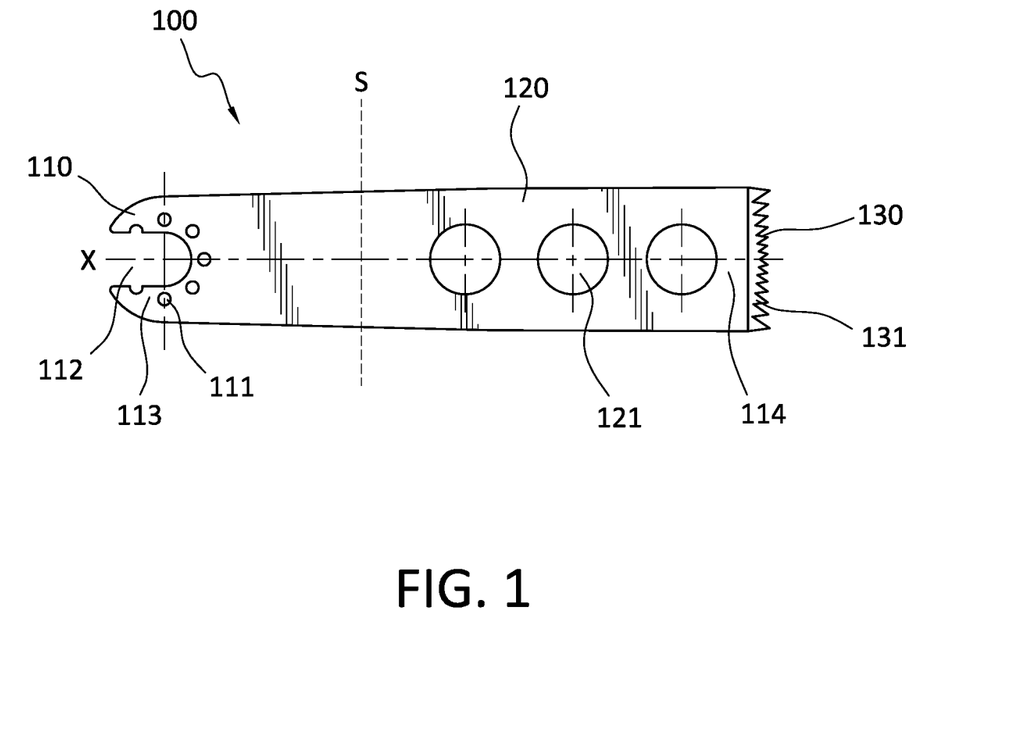
FIG. 1 illustrates a top view of an embodiment of the saw blade.

FIG. 1 illustrates an embodiment of the saw blade 100. The saw blade 100 includes a coupling 110 at a proximal end 113. In this embodiment, the coupling 110 includes a plurality of holes 111 and a U-shaped cutout 112 configured to connect a blade body 120 to a handpiece 1050, shown in FIG. 10. However, the coupling 110 may be configured in any geometry, including those shown in FIGS. 8A-8D, that allows for attachment of the blade body 120 to a handpiece 1050. The blade body 120, may also be configured in any geometry, including those shown in FIGS. 9A-9D, that allows for optimal weight and rigidity of the saw blade 100. The handpiece 1050 is adapted to oscillate the blade body 120. The saw blade 100 additionally includes a cutting edge 130 at a distal end 114 including a plurality of teeth 131. The blade body 120 may include a plurality of holes 121 extending longitudinally along axis X of the saw blade 100 that allows for mass reduction of the saw blade 100, and consequent decrease in vibration, noise load, and mechanical load of the saw blade 100.

Figure 2A:
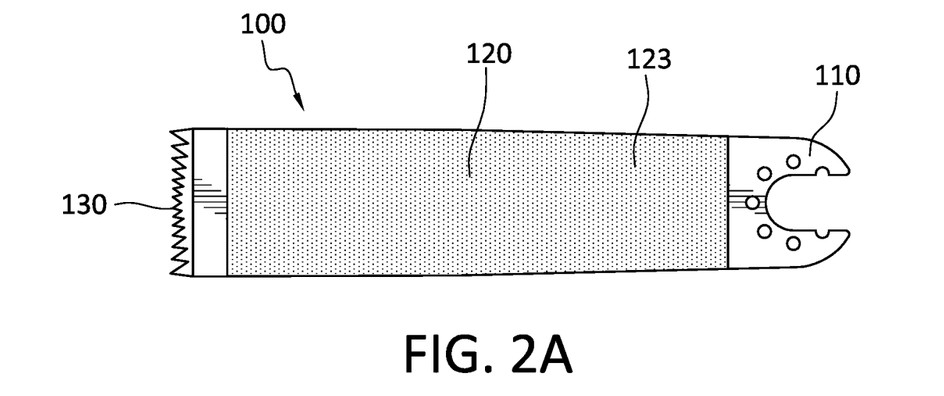
FIGS. 2A-C illustrate a top view of embodiments of the saw blade that include a blade body including a composite material.

FIG. 2A illustrates a top view of another embodiment of the saw blade 100 that includes a continuous blade body 120, wherein the blade body 120 includes a top surface 123 that is manufactured from a different material than the coupling 110 and the cutting edge 130.

In various embodiments, the top surface of the blade body 120 may be manufactured from a composite hybrid material, defined as a material made of two or more materials bonded together under high pressure and temperature. In various embodiments, the blade body 120 may include a carbon composite material. Suitable carbon composite materials include a matrix material, plastic, filling material, carbon fiber fabric material or combinations thereof. In some embodiments the carbon composite material includes a carbon fiber fabric material or combinations of carbon fiber fabric materials having different strengths to achieve an optimal stiffness of the saw blade 100. Suitable strength classes of the carbon fiber fabric materials include high tenacity (HI), very high tenacity (UHT), low modulus (LM), intermediate modulus (IM), high modulus (HM), ultra modulus (UM), ultra high modulus (UHM), ultra modulus strength (UMS), high modulus (HMS), and combinations thereof.

The coupling 110 and cutting edge 130 shown in FIG. 2A may be manufactured from a metal material such as steel, titanium, titanium/ceramic material and combinations thereof. In various embodiments, the top surface 123 may be joined to the coupling 110 and cutting edge 130 using any method known in the art used to join composite and metal materials to each other. Suitable methods include bonding using adhesive resins, and the like.

Figure 2B:
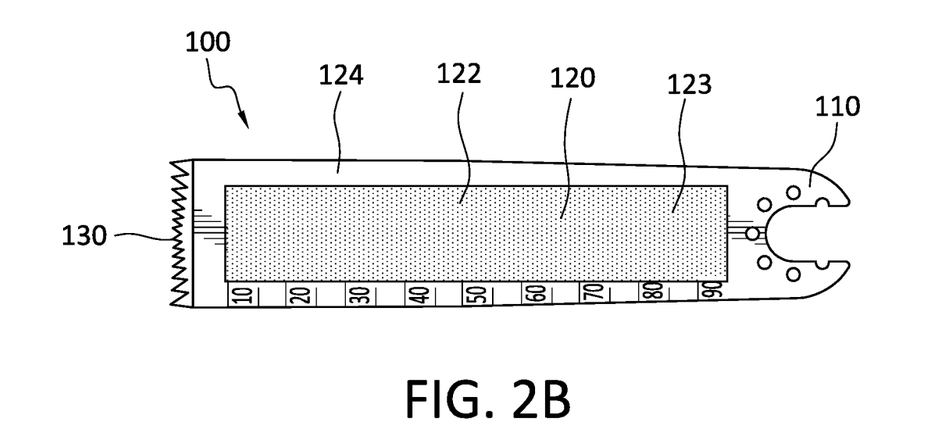

FIG. 2B illustrates a top view of another embodiment of the saw blade 100, wherein the top surface 123 of the blade body 120 includes a composite inlay portion 122 surrounded by a metal frame 124. In this embodiment, the metal frame 124 protects the composite inlay portion 122 from damage.

Figure 2C:
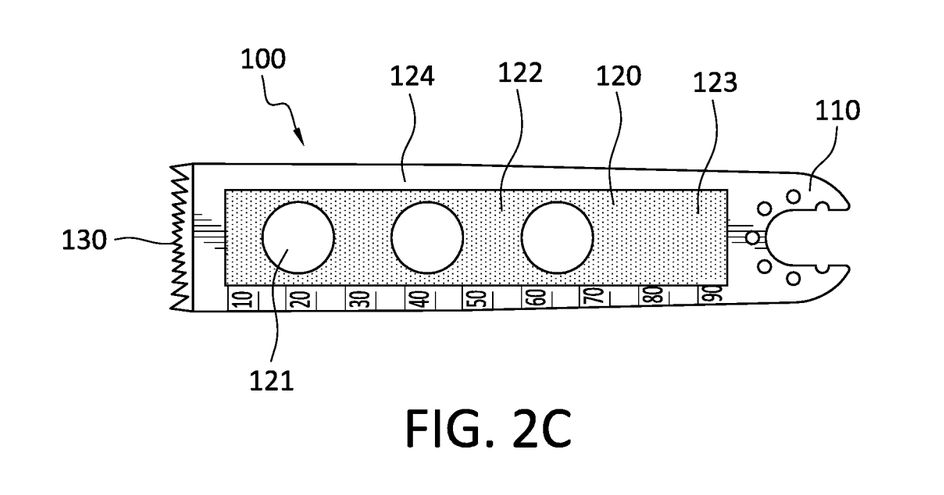

FIG. 2C illustrates a top view of another embodiment of the saw blade 100, wherein the composite inlay portion 122 includes a plurality of holes 121, that extend along a longitudinal axis of the composite inlay portion 122, for additional mass reduction.

Figure 3:
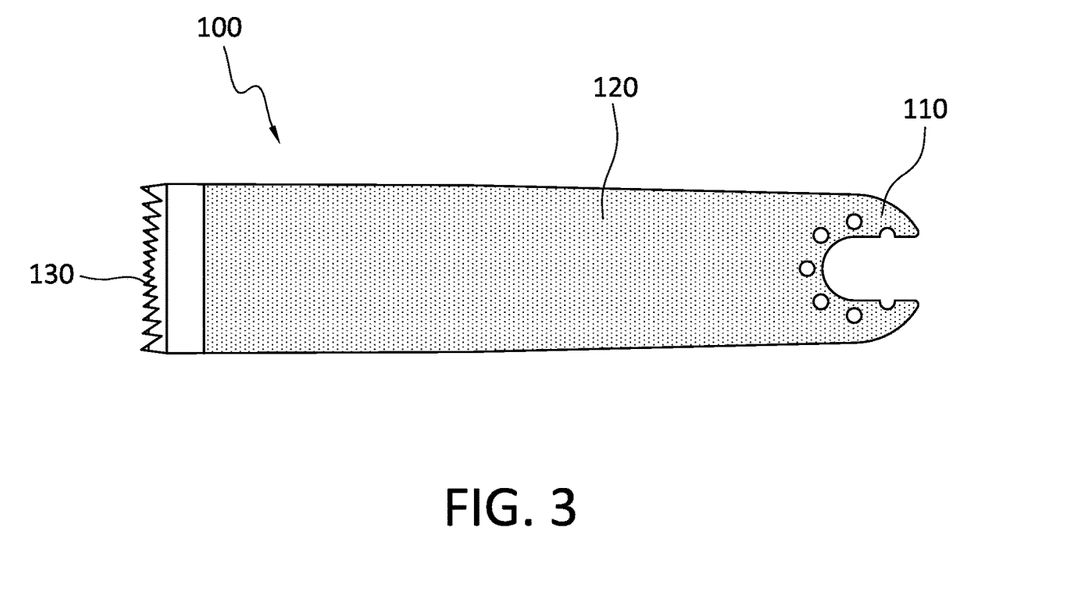
FIG. 3 illustrates a top view of another embodiment of the saw blade wherein the blade body and coupling both include a composite material.

FIG. 3 illustrates a top view of another embodiment of the saw blade 100. In this embodiment, the coupling 110 is also manufactured from a composite material.

Figure 4A:
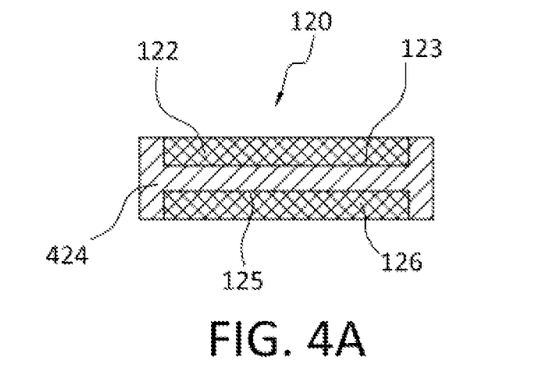
FIGS. 4A-F illustrate a cross-sectional view along line S in FIG. 1 of various embodiments of the blade body.

FIG. 4A illustrates a cross-sectional view along axis S of FIG. 1 of an embodiment of the blade body 120. In this embodiment, the blade body 120 includes a metal shaft 424 that includes cutouts on a top surface 123 and an opposing bottom surface 125 to accommodate a first composite inlay portion 122 positioned on the top surface 123 and a second composite inlay portion 126 positioned opposite the first composite inlay portion 122 on the bottom surface 125.

Figure 4B:
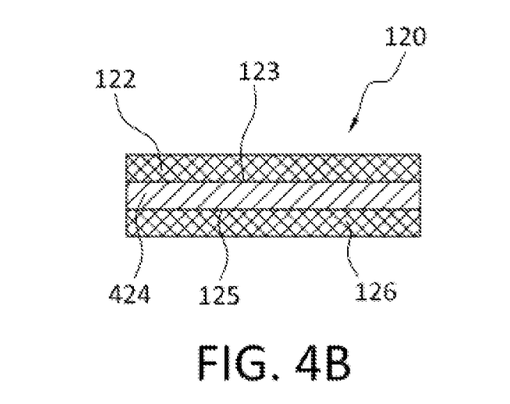

FIG. 4B illustrates a cross-sectional view along axis S of FIG. 1 of a second embodiment of the blade body 120. In this embodiment, the blade body 120 includes a metal shaft 424. The first composite inlay portion 122 is layered on a top surface 123 of the metal shaft 424 so as to completely cover the top surface 123 and the second composite inlay portion 126 is layered on a bottom surface 125 of the metal shaft 124 so as to completely cover the bottom surface 125.

Figure 4C:
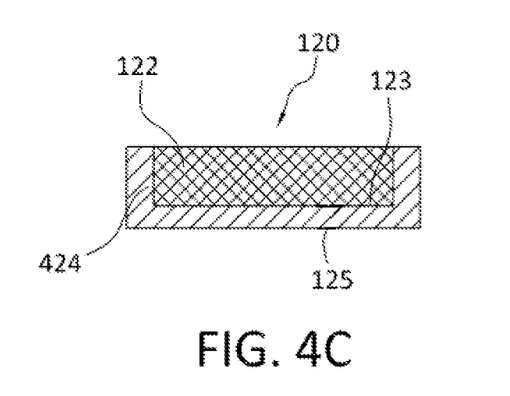

FIG. 4C illustrates a cross-sectional view along axis S of FIG. 1 of a third embodiment of the blade body 120. In this embodiment, the blade body 120 includes a metal shaft 424 that includes a cutout to accommodate a single composite inlay portion 122 on a top surface 123.

Figure 4D:
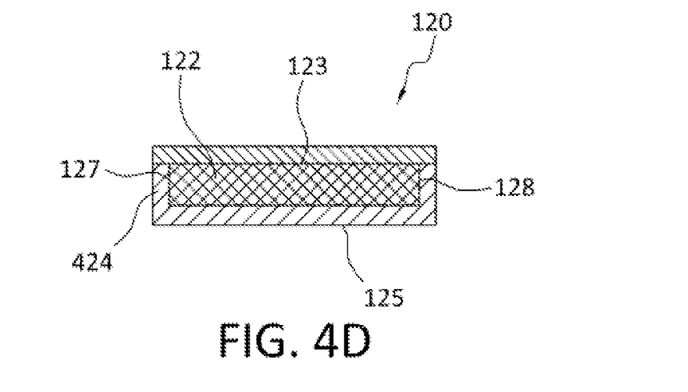

FIG. 4D illustrates a cross-sectional view along axis S of FIG. 1 of a fourth embodiment of the blade body 120. In this embodiment, the composite inlay portion 122 is surrounded on a top surface 123, a bottom surface 125, a first side surface 127 and a second side surface 128 by a metal shaft 424.

Figure 4E:
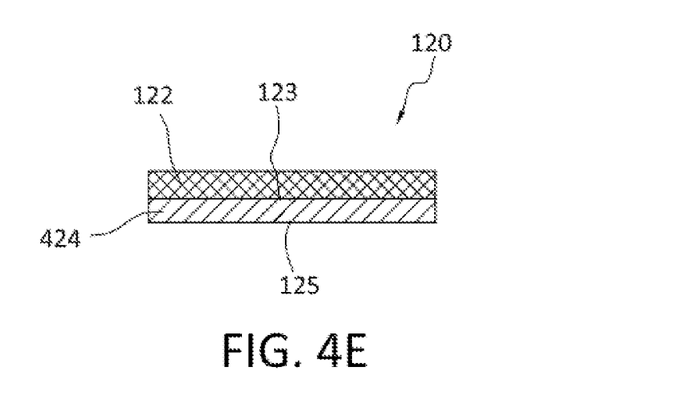

FIG. 4E illustrates a cross-sectional view along axis S of FIG. 1 of a fifth embodiment of the blade body 120. In this embodiment, the blade body 120 includes a metal shaft 424. The composite inlay portion 122 is layered on a top surface 123 of the metal shaft 424 so as to completely cover the top surface 123.

Figure 4F:
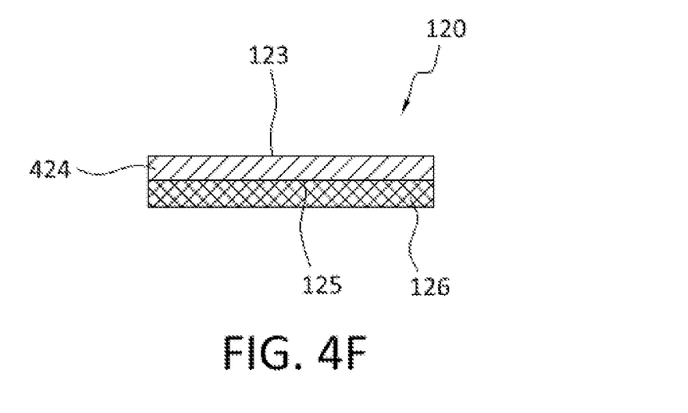

FIG. 4F illustrates a cross-sectional view along axis S of FIG. 1 of a sixth embodiment of the blade body 120. In this embodiment, the blade body 120 includes a metal shaft 424. The composite inlay portion 126 is layered on a bottom surface 125 of the metal shaft 424 so as to completely cover the bottom surface 125.

In various embodiments, the saw blade 100 has a usable length of between about 70 mm to about 90 mm, a total length of about 95 mm to about 120 mm and width of about 20 mm to about 25 mm. The saw blade 100 preferably has a thickness of about 2.00 mm. The thickness of the saw blade 100 may be from 1 mm to 3 mm, from 1.5 mm to 2.5 mm, from 1.9 mm to 2.2 mm, or other thicknesses. The saw blade 100 is further characterized by a deflection value of about 6 mm to about 9 mm, and a mass moment of inertia of about 50 kg*mm$^2$ to about 110 kg*mm$^2$.

In various embodiments, the saw blade 100 is configured to limit flexing (e.g. as a result of skiving) of the saw blade 100 to about 0.25 mm or less upon application of a 2.2N load, preferably 0.2 mm or less, preferably about 0.15 mm or less. In various embodiments, the saw blade 100 is characterized by a weight low enough to achieve the flexing limit of 0.25 mm or less upon application of a 2.2N load, as described herein.

Figure 5A:
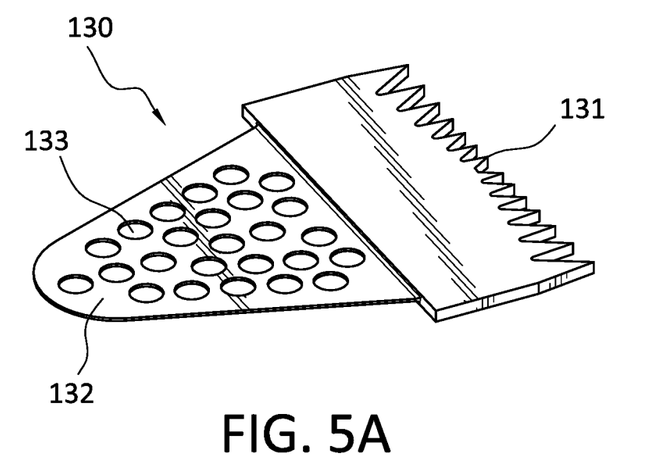
FIGS. 5A-B illustrate perspective views of embodiments of the cutting edge of the saw blade.

FIG. 5A illustrates a perspective view of an embodiment of the cutting edge 130. The cutting edge 130 includes a plurality of teeth 131 and a connector 132 which includes a plurality of holes 133 distributed therethrough. During manufacture of the saw blade 100, composite material may be filled into the plurality of holes 133 to allow for mechanical interlocking of the cutting edge 130 with the blade body 120. In another embodiment, the connector 132 may be roughened and/or activated with primers or treated in such a way as to allow for mechanical interlocking of the cutting edge 130 with the blade body 120. Suitable treatment procedures may include surface activation and/or structuring procedures, such as plasma surface activation, UV surface cleaning and UV surface activation, plasma etching, fluorination, etching with acid to increase surface roughness, abrasive blasting to increase surface roughness, laser surface activation or structuring, or combinations thereof.

Figure 5B:
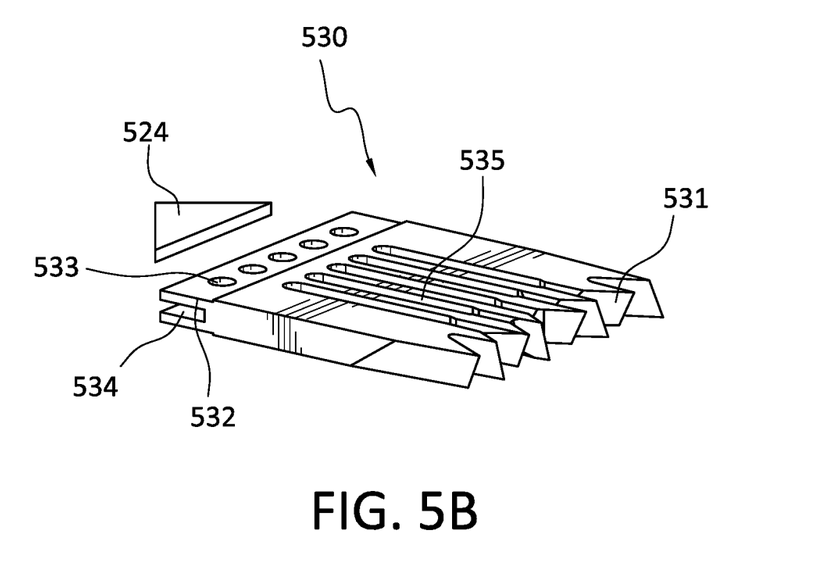
Figure 5C:
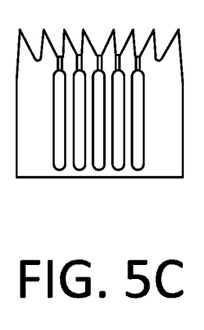
FIGS. 5C-E illustrate top views of other embodiments of the cutting edge of the saw blade.
Figure 5D:
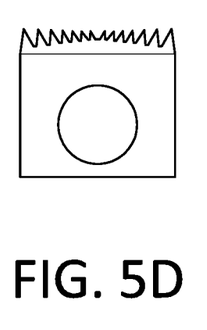
Figure 5E:
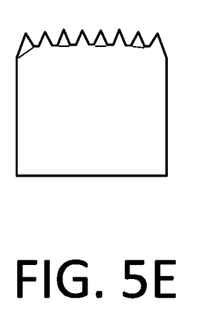
Figure 5F:
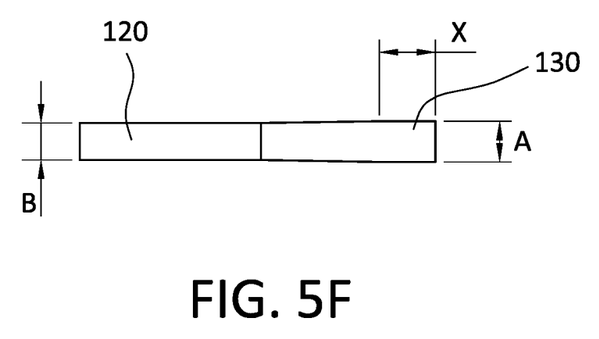
FIG. 5F illustrates a cross-sectional side view of the blade body and the cutting edge of the saw blade.

FIG. 5B illustrates a perspective view of another embodiment of the cutting edge 530. The cutting edge 530 includes a plurality of teeth 531 and a connector 532. The cutting edge 530 may further include a plurality of grooves 535 configured to aid in ejection of debris, e.g. bone chips, during use of the blade. The connector 532 includes a plurality of holes 533 distributed longitudinally along an axis of the connector 532 parallel to a saw blade shaft 524. During manufacture of the saw blade 100, composite material may be filled in the plurality of holes 533 to allow for mechanical interlocking of the cutting edge 530 with a blade body 120. In this embodiment, the cutting edge 530 additionally includes a slot 534 configured to slidably receive the saw blade shaft 524. FIGS. 5C-E illustrate other embodiments of the cutting edge 130. Additionally, in various embodiments, as shown in FIG. 5F, the thickness of the cutting edge 130 may be greater than the thickness of the blade body 120.

In various embodiments, the connectors 132, 532 may have any geometry that allows for optimal weight and rigidity of the saw blade 100. In various embodiments, the plurality of teeth 131,531 may further have any geometry that allows for optimal functionality of the saw blade 100.

Figure 6A:
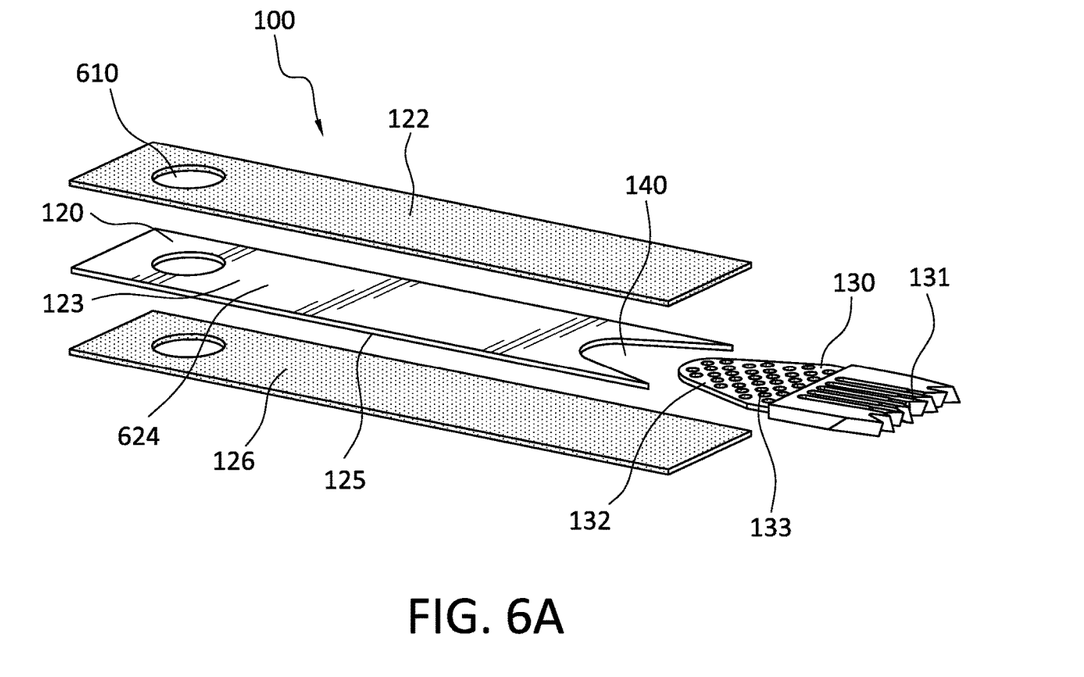
FIG. 6A illustrates an exploded perspective view of an embodiment of the saw blade that includes a blade body completely manufactured from a composite material, and a cutting edge.
Figure 10:
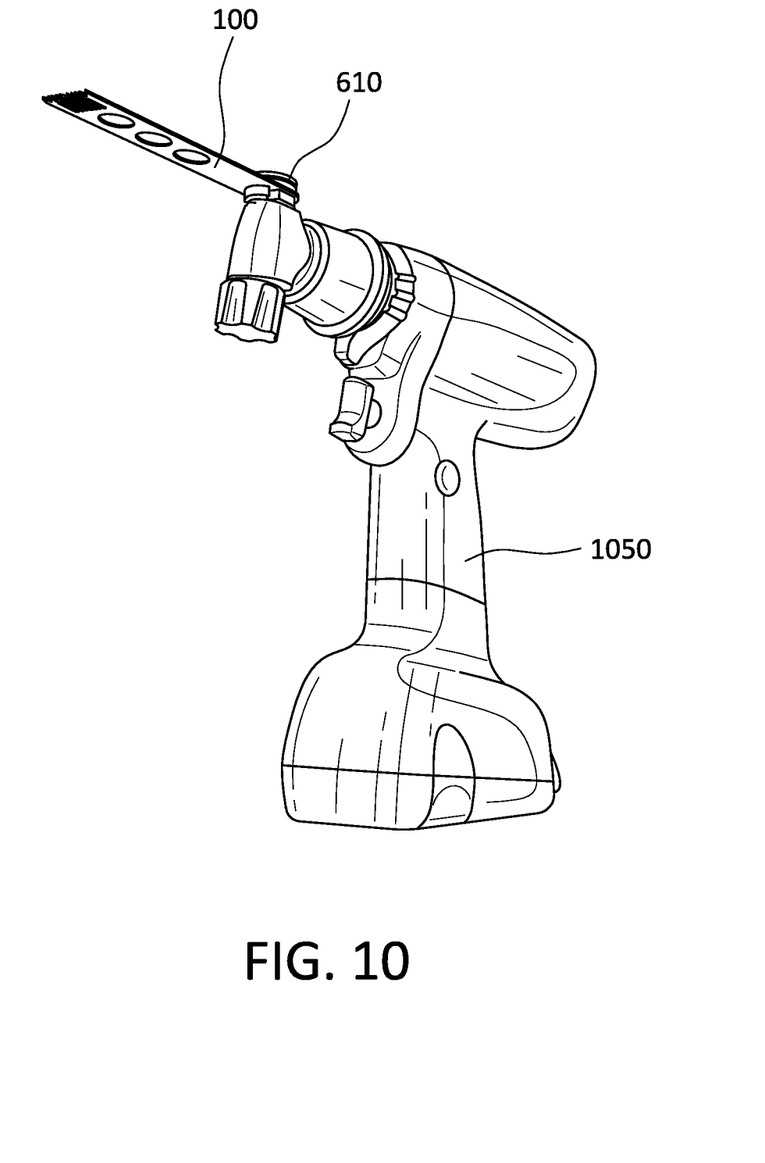
FIG. 10 illustrates a perspective view of the saw blade coupled to a handpiece.

FIG. 6A illustrates another embodiment of a saw blade 100 that includes a blade body 120 completely manufactured from a composite material, and a cutting edge 130. The blade body 120 includes a first composite inlay portion 122, layered on a top surface 123 of a saw blade shaft 624, also manufactured from a composite material, so as to completely cover the top surface 123, and a second composite inlay portion 126 layered on a bottom surface 125 of the saw blade shaft 624, opposite the first composite inlay portion 122, so as to completely cover the bottom surface 125, as shown in more detail in FIG. 6B. The blade body 120, further includes a coupling hole 610 configured to couple the saw blade 100 to a handpiece 1050, as shown in FIG. 10. As shown in FIG. 6A, the cutting edge 130 is merged with the saw blade shaft 624 using a connector 132, which is received within a U-shaped cutout 140, located at a distal end of the saw blade shaft 624.

Figure 6B:
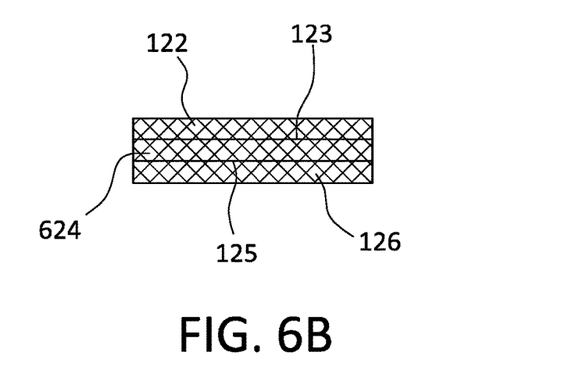
FIG. 6B illustrates a cross-sectional side view of the saw blade shown in FIG. 6A.

In various embodiments, the first composite inlay portion 122 and second composite inlay portion 126 may be manufactured from the same composite material. In other embodiments the first composite inlay portion 122 and second composite inlay portion 126 may be manufactured using different composite materials. In various embodiments, the saw blade shaft 624 may alternatively be manufactured using other materials, such as unreinforced PEEK, and the like.

Figure 7A:
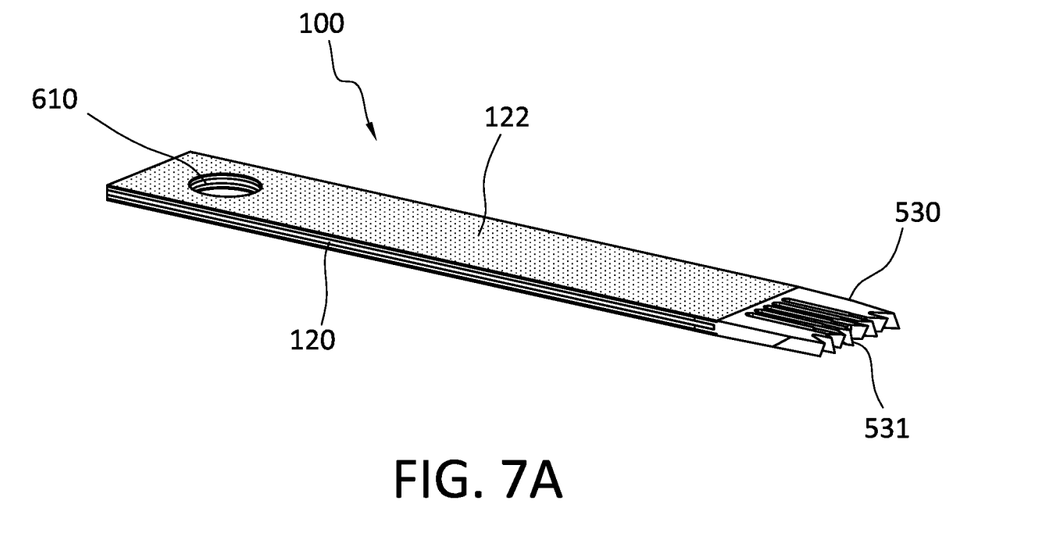
FIGS. 7A-B illustrate a perspective view and an exploded perspective view of another embodiment of the saw blade that includes a blade body including a composite material and a cutting edge.

FIG. 7A illustrates another embodiment of a saw blade 100 that includes a coupling hole 610, a blade body 120 and a cutting edge 530. As shown in more detail in FIGS. 7B and 7C, the blade body 120 includes a first composite inlay portion 122 layered on a top surface 762 of a first intermediate composite inlay portion 760 so as to completely cover the top surface 762 of the first intermediate composite inlay portion 760. The blade body 120 additionally includes a second composite inlay portion 126 layered on a bottom surface 763 of a second intermediate composite inlay portion 761, opposite the first composite inlay portion 122, so as to completely cover the bottom surface 763 of the second intermediate composite inlay portion 761. The first intermediate composite inlay portion 760 is layered on a top surface 123 of a saw blade shaft 724, so as to completely cover the top surface 123 of the saw blade shaft 724. The second intermediate composite inlay portion 761 is layered on a bottom surface 125 of the saw blade shaft 724, opposite the first intermediate composite inlay portion 760, so as to completely cover the bottom surface 125 of the saw blade shaft 724. In various embodiments, the first composite inlay portion 122, second composite inlay portion 126, first intermediate composite inlay portion 760 and second intermediate composite inlay portion 761, may be manufactured from the same composite material. In other embodiments, the first composite inlay portion 122, second composite inlay portion 126, first intermediate composite inlay portion 760 and second intermediate composite inlay portion 761 may each be manufactured from different composite materials. In various embodiments, the first composite inlay portion 122, second composite inlay portion 126, first intermediate composite inlay portion 760 and second intermediate composite inlay portion 761 may be manufactured using composite materials of any grade that would allow for optimal weight and rigidity of the saw blade 100. In various embodiments, the saw blade shaft 724 may be manufactured from a metallic or composite material as described herein.

Figure 7B:
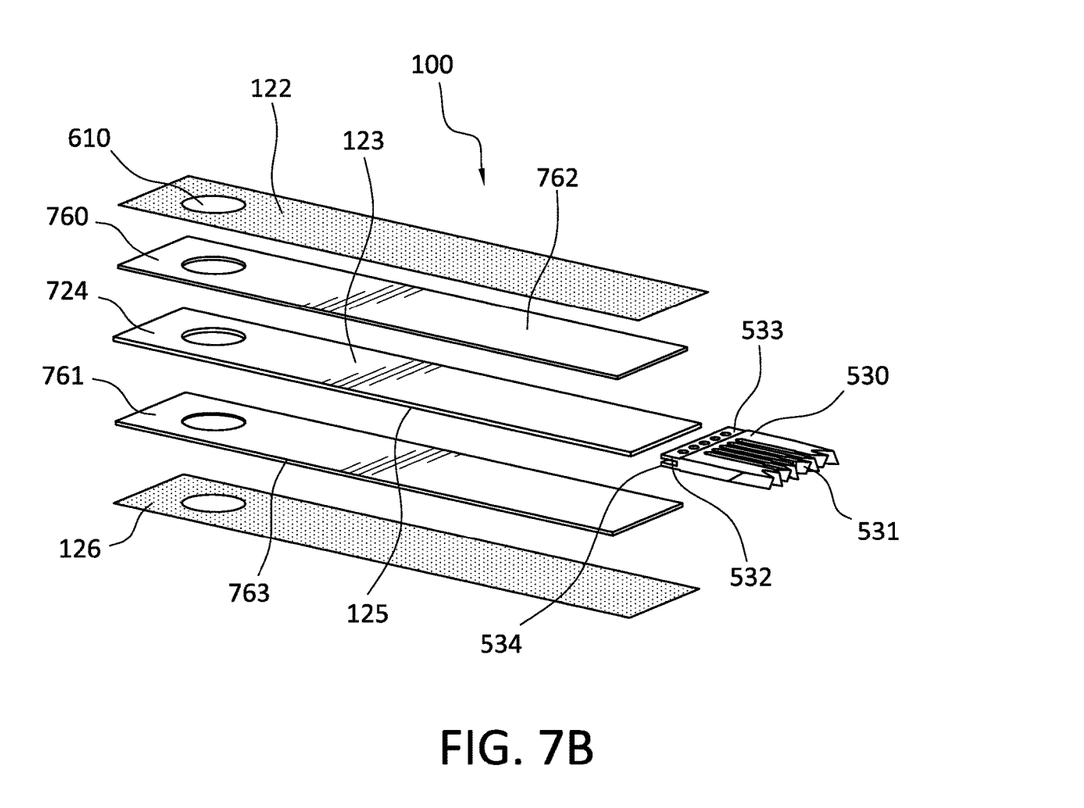
Figure 7C:
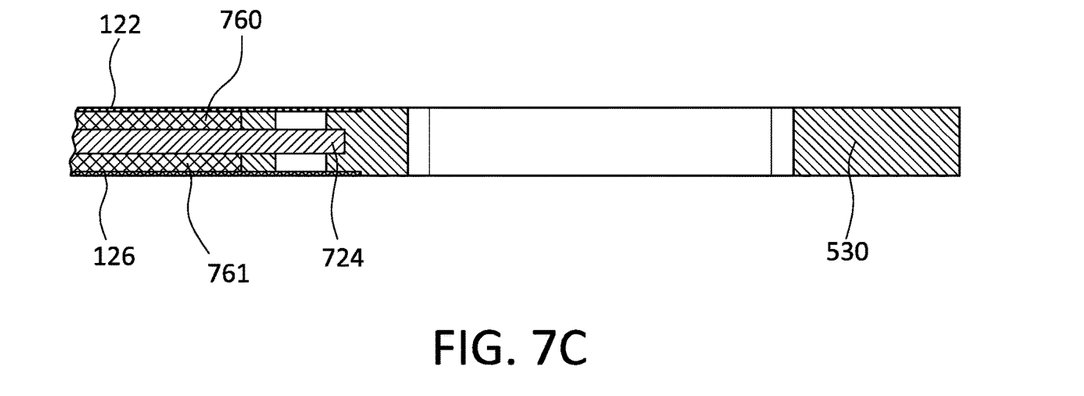
FIG. 7C illustrates a cross-sectional side view of the embodiment of the saw blade shown in FIGS. 7A-B.

In some embodiments, the first composite inlay portion 122 and second composite inlay portion 126 may be manufactured using an unreinforced PEEK material. In some embodiments, the first intermediate composite inlay portion 760 and second intermediate composite inlay portion 761 may be manufactured using a unidirectional laminate material.

Figure 7D:
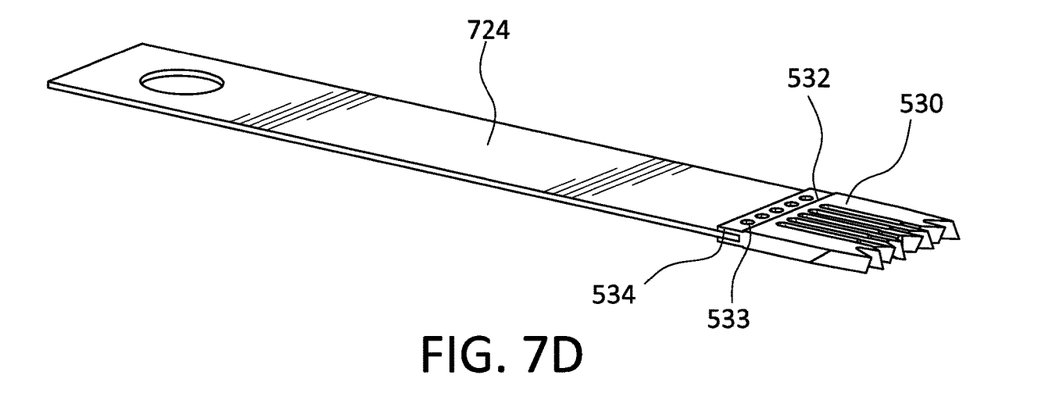
FIG. 7D illustrates a perspective component view of the saw blade shaft and cutting edge of the saw blade of FIGS. 7A-7C manufactured from different materials.

As shown in FIG. 7D, the saw blade shaft 724 may be merged with the cutting edge 530 by sliding the saw blade shaft 724 into slot 534 located on the connector 532. In the embodiment of FIG. 7D, the saw blade shaft 724 and cutting edge 530 may be made from the same material, e.g. stainless steel, or different materials, e.g. aluminum, titanium, ceramic, in any combination as known to a person of ordinary skill in the art to produce a saw blade 100 of optimal weight and rigidity. In various embodiments, the saw blade shaft 724 and cutting edge 530 may further be heat treated independently from each other to confer optimal properties.

In various embodiments, the saw blade shaft 724 may be merged with the cutting edge 530 using any suitable merging method known to a person of ordinary skill in the art. Suitable merging methods include welding methods, such as laser welding, electrode beam welding, press-welding, friction welding and the like. In further embodiments, the plurality of holes 533 located on the connector 532 may be used for welding purposes with the saw blade shaft 724, or may be used for mechanical interlocking with the composite layers 722, 760, 761, 726.

Figure 7E:
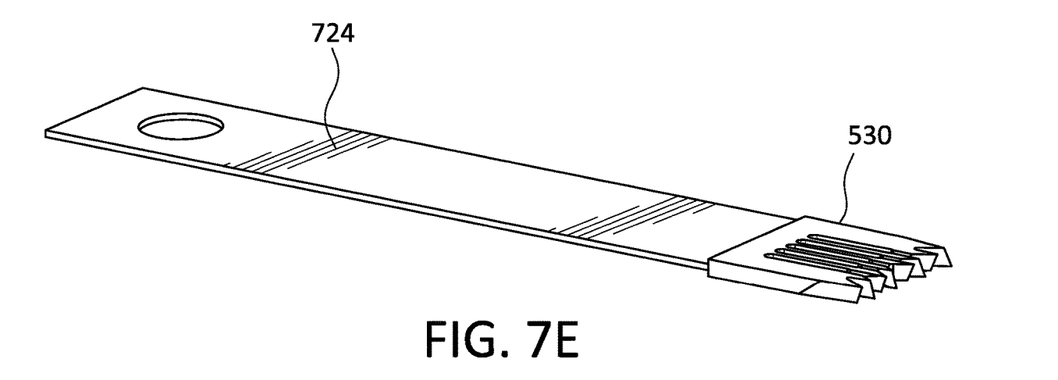
FIG. 7E illustrates a perspective component view of the saw blade shaft and cutting edge of the saw blade of FIGS. 7A-7C manufactured from the same materials.
Figure 8A:
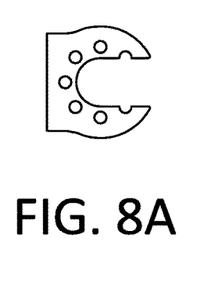
FIGS. 8A-D illustrate top views of various embodiments of the coupling.
Figure 8B:
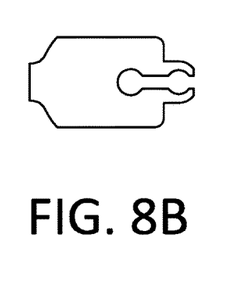
Figure 8C:
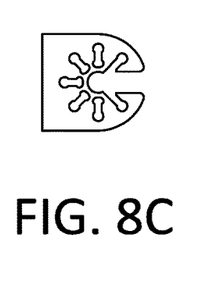
Figure 8D:
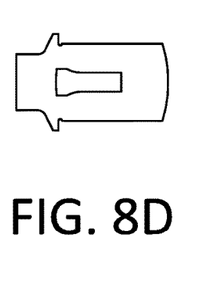
Figure 9A:
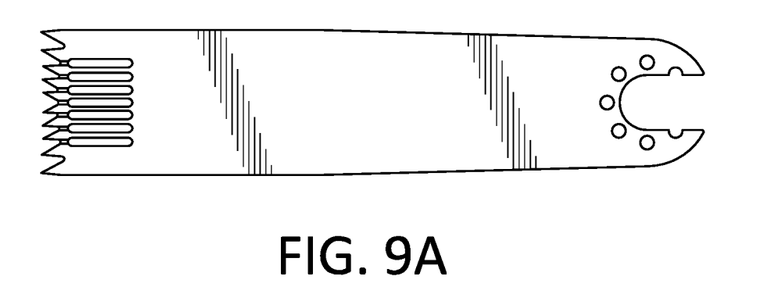
FIGS. 9A-D illustrate top views of various alternative embodiments of the blade body.
Figure 9B:
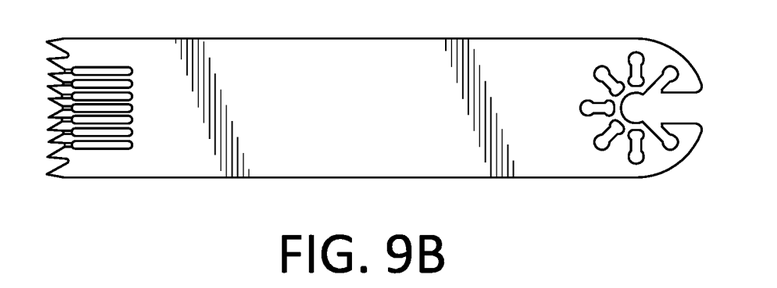
Figure 9C:
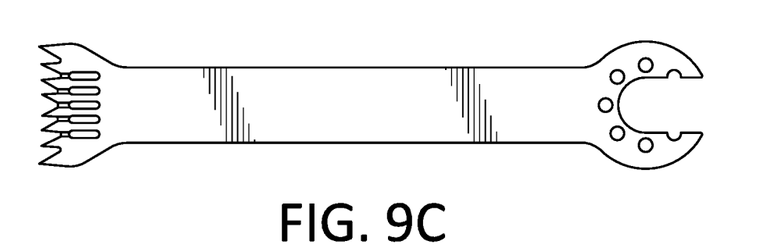
Figure 9D:
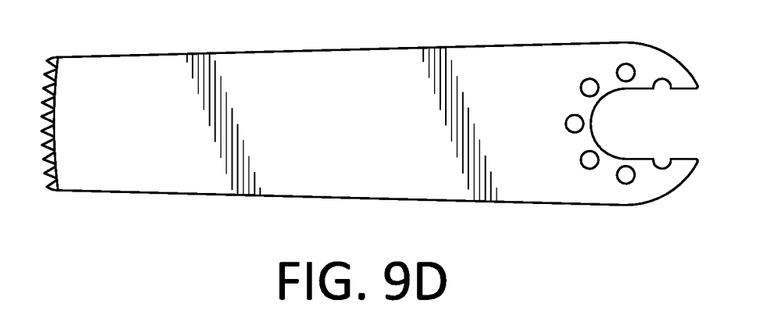

As shown in FIG. 7E, the saw blade shaft 724 and cutting edge 530 may also be manufactured as a single piece from the same material.

FIG. 10 illustrates in more detail, the saw blade 100 coupled using coupling hole 610 to a handpiece 1050.

Various features and structures are illustrated throughout the various embodiments described above in specific combinations of those features and structures. These various features and structures may also be combined into other specific combinations not explicitly shown and still be within the scope of the invention disclosed herein.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be effected while remaining within the spirit and scope of the invention. Further, various elements from the various embodiments may be combined to form other embodiments that are within the spirit and scope of the invention. Accordingly, the foregoing disclosure, description, and figures are for illustrative purposes only and do not in any way limit the invention, which is defined only by the claims.

What is claimed is:

1. A saw blade comprising
a blade body having a top surface and a bottom surface, wherein the blade body is at least partially comprised of a first composite material;
a cutting edge on a distal end of the blade body; and
a coupling configured to connect the blade body to a handpiece adapted to oscillate the blade body,
wherein at least one of the top surface and the bottom surface of the blade body comprises an inlay portion comprising a second composite material; and
the inlay portion further comprises holes extending along a longitudinal axis of the blade body.

2. The saw blade of claim 1, wherein the inlay portion is surrounded on all sides by a metal frame.

3. The saw blade of claim 2, wherein the metal frame comprises steel.

4. The saw blade of claim 1, wherein both the blade body and the coupling at least partially comprise the first composite material.

5. The saw blade of claim 1, wherein the saw blade further comprises at least two of the materials selected from the group consisting of steel, polymer, titanium and ceramic.

6. The saw blade of claim 1, wherein the first composite material is selected from the group consisting of a matrix material, a plastic material, a filling material and a carbon fiber fabric material.

7. The saw blade of claim 6, wherein the first composite material is a carbon fiber fabric material.

8. The saw blade of claim 1, wherein the cutting edge comprises a connector configured to mechanically interlock the cutting edge with the blade body.

9. The saw blade of claim 8, wherein the connector comprises a plurality of holes configured to mechanically interlock with the first composite material of the blade body.

10. A saw blade comprising
a blade body having a top surface and a bottom surface, wherein the blade body is at least partially comprised of a first composite material;
a cutting edge on a distal end of the blade body; and
a coupling configured to connect the blade body to a handpiece adapted to oscillate the blade body,
wherein at least the top surface is a planar surface;
wherein the top surface of the blade body comprises an inlay portion comprising a second composite material;
wherein the inlay portion comprises holes extending along a longitudinal axis of the blade body.

* * * * *